(12) United States Patent
Hsiung et al.

(10) Patent No.: US 10,136,848 B2
(45) Date of Patent: Nov. 27, 2018

(54) DEVICE AND SYSTEM OF BLOOD COLLECTION, AND METHOD THEREOF

(71) Applicant: Winnoz Technology, Inc., Taipei (TW)

(72) Inventors: Le-Chang Hsiung, Taipei (TW); Fang-Yu Lin, Taipei (TW); Jui-Shuan Wu, Taipei (TW); Li-Tseng Ou, Taipei (TW); Po-Chun Chen, Taipei (TW); Chuan Whatt Eric Ou, Singapore (SG)

(73) Assignee: Winnoz Technology, Inc., Taipei (TW)

( * ) Notice: Subject to any disclaimer, the term of this patent is extended or adjusted under 35 U.S.C. 154(b) by 0 days.

(21) Appl. No.: 15/160,051

(22) Filed: May 20, 2016

(65) Prior Publication Data
US 2017/0332954 A1 Nov. 23, 2017

(51) Int. Cl.
*A61B 5/15* (2006.01)
*A61B 5/00* (2006.01)

(52) U.S. Cl.
CPC .. *A61B 5/150022* (2013.01); *A61B 5/150099* (2013.01); *A61B 5/150343* (2013.01); *A61B 5/6848* (2013.01)

(58) Field of Classification Search
CPC .............. A61B 5/14532; A61B 5/7275; A61B 10/0045
USPC ................................................ 600/573, 583
See application file for complete search history.

(56) References Cited

U.S. PATENT DOCUMENTS

| | | | | |
|---|---|---|---|---|
| 7,258,673 B2* | 8/2007 | Racchini | ............ | A61B 5/15087 600/583 |
| 7,740,581 B2* | 6/2010 | Buse | ................... | A61B 5/1411 600/347 |
| 7,896,830 B2* | 3/2011 | Gura | ...................... | A61M 1/16 210/645 |
| 8,808,202 B2* | 8/2014 | Brancazio | ............ | A61B 5/1411 600/576 |
| 9,033,898 B2* | 5/2015 | Chickering, III | .... | A61B 5/1411 600/573 |

(Continued)

FOREIGN PATENT DOCUMENTS

| | | |
|---|---|---|
| CN | 1551802 | 12/2004 |
| CN | 104644437 | 5/2015 |

(Continued)

OTHER PUBLICATIONS

International Search Report for International Application No. PCT/CN2017/084838 dated Jul. 28, 2017, 5 pages.

(Continued)

*Primary Examiner* — May Abouelela

(74) *Attorney, Agent, or Firm* — Amin, Turocy & Watson LLP

(57) ABSTRACT

A device for collecting a blood sample is provided. The device includes a collection unit, at least one capillary tube, a vacuum connector, and a storage unit. The collection unit has a top window for receiving the blood sample, a top surface, and a channel communicated with the top window. The at least one capillary tube is disposed in the collection unit and has a top end adjacent to the top window of the collection unit. The vacuum connector extends from the collection unit and communicates with the channel to provide a negative pressure by removing air in the channel. The storage unit is disposed under the collection unit for storing the blood sample.

27 Claims, 14 Drawing Sheets

(56) References Cited

U.S. PATENT DOCUMENTS

| | | | | |
|---|---|---|---|---|
| 9,041,541 | B2* | 5/2015 | Levinson | G06F 19/3456 340/539.12 |
| 9,113,836 | B2* | 8/2015 | Bernstein | A61B 5/1438 |
| 9,295,417 | B2* | 3/2016 | Haghgooie | A61B 5/1411 |
| 2003/0143746 | A1* | 7/2003 | Sage, Jr. | A61B 5/14525 436/8 |
| 2006/0116607 | A1* | 6/2006 | Nakamura | A61B 5/14532 600/583 |
| 2007/0105176 | A1* | 5/2007 | Ibey | C12Q 1/54 435/14 |
| 2007/0213638 | A1* | 9/2007 | Herbrechtsmeier | A61B 5/15186 600/583 |
| 2008/0221407 | A1* | 9/2008 | Baker | A61B 5/14514 600/309 |
| 2009/0043227 | A1* | 2/2009 | Fujiwara | A61B 5/14532 600/583 |
| 2009/0216103 | A1* | 8/2009 | Brister | A61B 5/14532 600/347 |
| 2010/0234768 | A1* | 9/2010 | Uchiyama | A61B 5/15134 600/583 |
| 2011/0125059 | A1* | 5/2011 | Petrich | A61B 5/1411 600/583 |
| 2011/0172559 | A1* | 7/2011 | Fei | A61B 5/1411 600/583 |
| 2012/0041338 | A1* | 2/2012 | Chickering, III | A61B 5/14514 600/575 |
| 2015/0208973 | A1* | 7/2015 | Burkholz | A61B 5/1405 600/581 |
| 2015/0212006 | A1* | 7/2015 | Emery | A61B 5/14532 600/583 |
| 2016/0100784 | A1* | 4/2016 | Kashmirian | A61B 5/15003 600/573 |

FOREIGN PATENT DOCUMENTS

| | | |
|---|---|---|
| CN | 205072874 | 3/2016 |
| CN | 205072879 | 3/2016 |
| WO | 03/094770 | 11/2003 |
| WO | 2013/101952 | 7/2013 |

OTHER PUBLICATIONS

Written Opinion for for International Application No. PCT/CN2017/084838 dated Jul. 28, 2017, 5 pages.

* cited by examiner

DEVICE AND SYSTEM OF BLOOD COLLECTION, AND METHOD THEREOF

BACKGROUND OF THE DISCLOSURE

1. Field of the Disclosure

The present disclosure relates to a blood collection and delivery system, particularly a system performing blood collection while preventing blood from coagulation.

2. Description of the Related Art

Currently, some methods have been used for collecting blood from a body. One of them is using a syringe to draw blood. However, this common method has some disadvantages. For example, it is highly risky for an untrained person to collect blood by using a syringe because it may cause unexpected injuries. Furthermore, it would not be appropriate to use a conventional syringe for blood drawing under some extreme conditions, for instance, in a micro-gravitational environment.

In addition, owing to diagnostic needs for fingertip blood, various existing means are commonly provided for delivery of fingertip blood. One of main challenges to deliver fingertip blood is that the amount of fingertip blood is usually too small to deliver. Most commonly, capillary tubes are used for fingertip blood delivery. Nevertheless, when more fingertip blood is required, more capillary tubes will be consumed. Moreover, since capillary tubes are usually fragile, they might be damaged during a delivery, which may cause sample contamination.

Although existing methods have been served as alternatives for blood collection, an easy-to-use device enabling drawing blood by any person at anywhere, especially at a space center with micro-gravity, is desirable. Moreover, a more reliable blood handling mechanism for a delivery of fingertip blood to a test site is favorable.

SUMMARY OF THE DISCLOSURE

The present disclosure provides a device for collecting a blood sample, which comprises a capillary tube and a negative pressure environment, such that the capillary tube is contacted with the blood drop from a puncture to continuously draw the blood by disrupting the surface tension of the blood drop avoiding blood coagulation. The negative pressure environment facilitates the bleeding of the puncture, such that a sufficient volume of the blood sample can be collected in a short time.

According to an aspect of the present disclosure, a device for collecting a blood sample is provided, the device comprises a collection unit comprising a top window for receiving the blood sample, a top surface, and a channel communicated with the top window; at least one capillary tube having a top end adjacent to the top window; a vacuum connector extended from the collection unit and communicated with the channel to provide negative pressure by removing air from the channel; and a storage unit disposed under the collection unit for storing the blood sample; wherein a distance between the top end of the at least one capillary tube and the top surface of the collection unit is in a range of 1.0 mm to 5.0 mm.

Another aspect of the present disclosure is a system for collecting a blood sample. The system comprises a cartridge and a docking station. The cartridge comprises a collection unit and a storage unit, and the docking station comprises a pressure control unit. The collection unit comprises a top window for receiving the blood sample, a top surface, a channel communicated with the top window, at least one capillary tube having a top end adjacent to the top window, and a vacuum connector extended from the collection unit and communicated with the channel. A distance between the top end of the at least one capillary tube and the top surface of the collection unit is in a range of 1.0 mm to 5.0 mm. The storage unit is disposed under the collection unit for storing the blood sample. The pressure control unit comprises a venting unit and a vacuum unit for creating an alternating negative pressure in the channel.

Moreover, the present disclosure further provides a method of collecting a blood sample, comprising: providing a collection unit having a top window for accommodating a puncture, a top surface and a channel communicated with the top window; providing at least one capillary tube in the collection unit having a top end adjacent to the top window for guiding a blood drop from the puncture to flow inside or along the at least one capillary tube, wherein a distance between the top end of the at least one capillary tube and the top surface of the collection unit is in a range of 1.0 mm to 5.0 mm; removing air from the channel through a vacuum connector to create a negative pressure in the channel; and storing the blood sample in a storage unit disposed underneath the collection unit.

These and other features and advantages of the device, system and method of the disclosure are described below with respect to illustrative embodiments of the disclosure.

| List of FIG. Labels | | | |
|---|---|---|---|
| 1 | collection unit | 11 | holder |
| 12 | vacuum connector | 122 | partition plate |
| 13 | funnel structure | 131 | space |
| 14 | capillary tube | 15 | pad |
| 16 | top window | 162 | top surface |
| 164 | bottom window | 17 | venting connector |
| 18 | channel | 2 | storage unit |
| 21 | sensor | 22 | storage channel |
| 24 | syringe-like storage unit | 241 | cap |
| 242 | barrel | 243 | stopper |
| 244 | absorbent material | 3 | pressure control unit |
| 31 | vacuum unit | 32 | venting unit |
| 4 | docking station | 41 | controller |
| 42 | power | 43 | puncturing mechanism |
| 44 | compression unit | 441 | passage |
| 442 | air cuff | 5 | blood sample, blood drop |
| 6 | cartridge | A | distance between a top surface and a top end of at least one capillary tube |

DETAILED DESCRIPTION OF THE DISCLOSURE

The following specific embodiments are provided to illustrate the present disclosure, the advantages and effects can be apparently understood by those skilled in the art after reading the disclosure of this specification.

It should be understood, in this specification the accompanying drawings depicted structure, proportion, size, etc., are disclosed only to match the content of the specification, to facilitate the understanding and reading of those skilled in the art, but not intend to limit the present disclosure in specific conditions, and do not have technical substantial meaning. Any modification of the structure, change of the ratio relation, or adjustment of the size should be involved in the scope of disclosures in this specification without influencing the producible efficacy and the achievable objective of this specification. Those changes or adjustments of relative relationship without substantial change of technical content should also be considered within the category of implementation.

Figure 1:
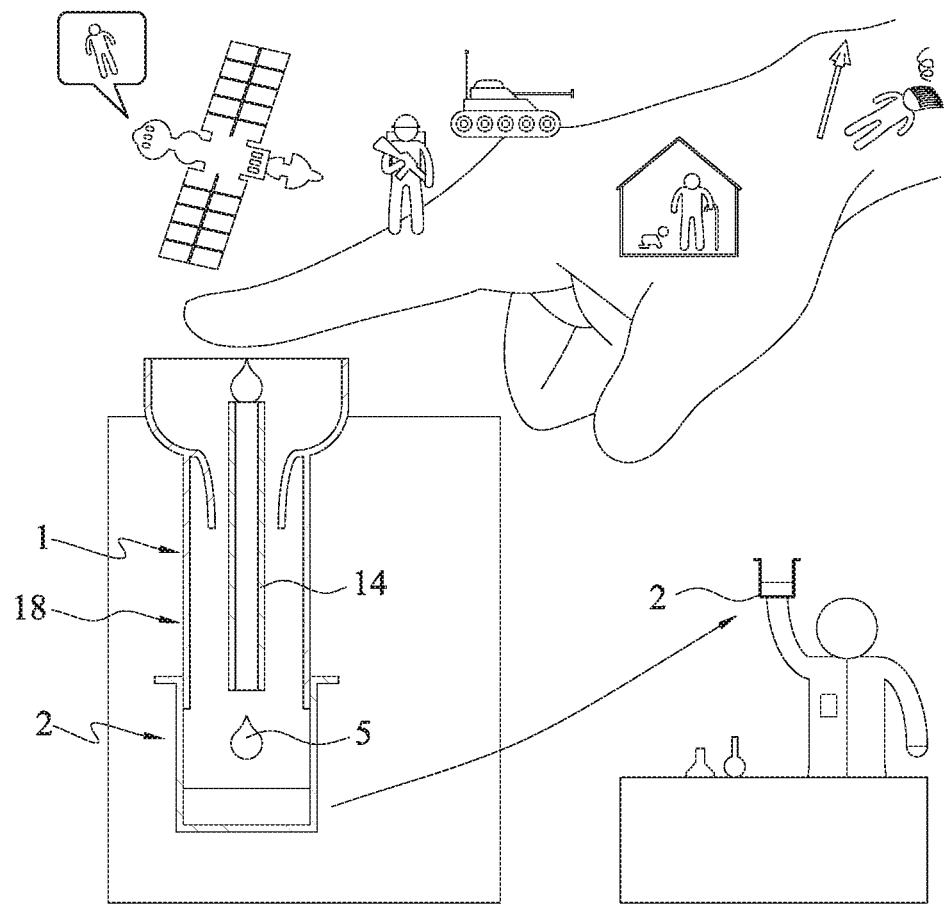
FIG. 1 is a conceptual drawing which illustrates the usage of the present disclosure occurring easily at anywhere and by any person in various conditions.

FIG. 1 shows a conceptual drawing which illustrates the usage of the present disclosure. The present disclosure can be easily used at anywhere and by any person in various conditions. For example, this disclosure can be used by soldiers in battlefields to collect blood samples (5) to determine whether the soldiers suffer from a biochemical attack, or by astronauts in a micro-gravity environment. In addition, this disclosure can be used to draw blood samples (5) of patients in areas which are distant from medical institutions for timely diagnoses. Moreover, this disclosure is applicable to homecare and laboratory uses etc. for various purposes.

Figure 2:
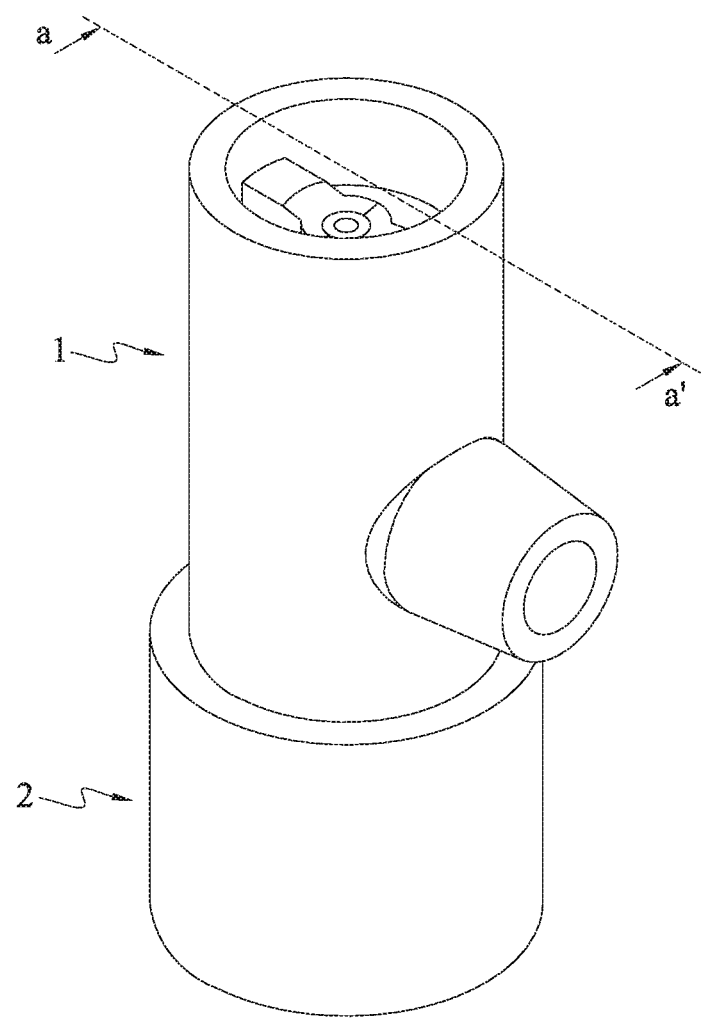
FIG. 2 illustrates a device for collecting a blood sample in accordance with a first embodiment of the present disclosure.
Figure 3:
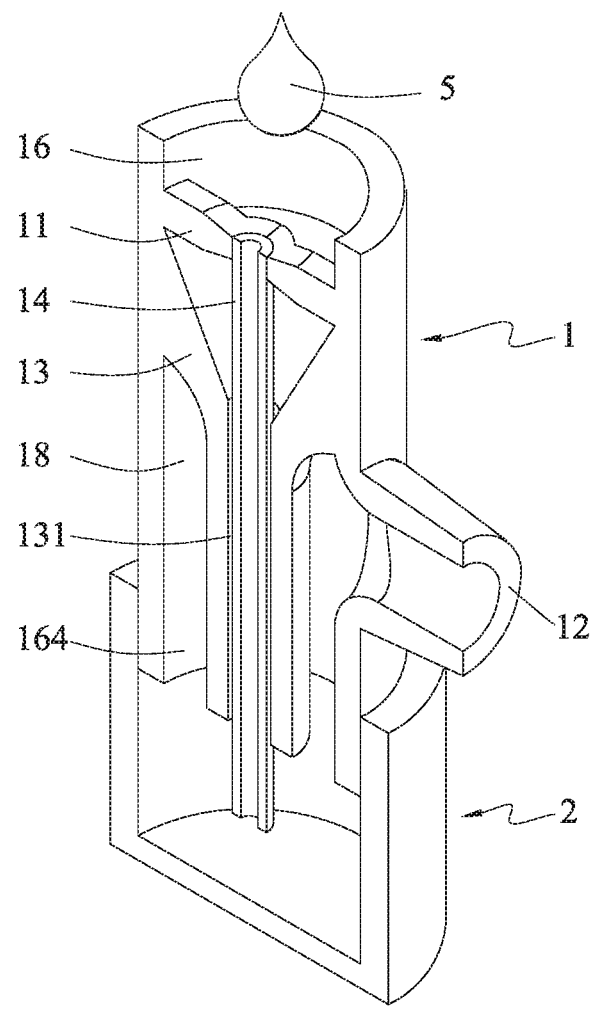
FIG. 3 illustrates an isometric view of the device along the line a-a' of FIG. 2.

FIGS. 2 and 3 show first embodiment of a blood collecting device. The device for collecting blood sample (5) comprises a collection unit (1) and a storage unit (2) mounted under the collection unit (1). The collection unit (1) is a structure comprising a top window (16), a bottom window (164), and a channel (18) communicated with the top window (16) and the bottom window (164). The collection unit (1) has a capillary tube (14) disposed in the collection unit (1), and a vacuum connector (12) extended outwardly from the collection unit (1). The collection unit (1) further comprises a holder (11) centrically formed in the channel (18) to hold the capillary tube (14) extended along a direction of the channel (18). The collection unit (1) further comprises a funnel structure (13) in the channel (18) for guiding the blood sample (5) into the storage unit (2). A space (131) is provided between the funnel structure (13) and the capillary tube (14). The storage unit (2) in this embodiment is a detachable cylindrical container mounted onto the bottom window (164) of the collection unit (1) for storing the blood sample (5). Herein, the storage unit (2) comprises a tube, a tank, a vessel, an analogue, or any combination thereof. Noticeably, an absorbent material (244, see FIG. 10) can be placed inside the storage unit (2) to absorb blood sample (5) collected.

Figure 4:
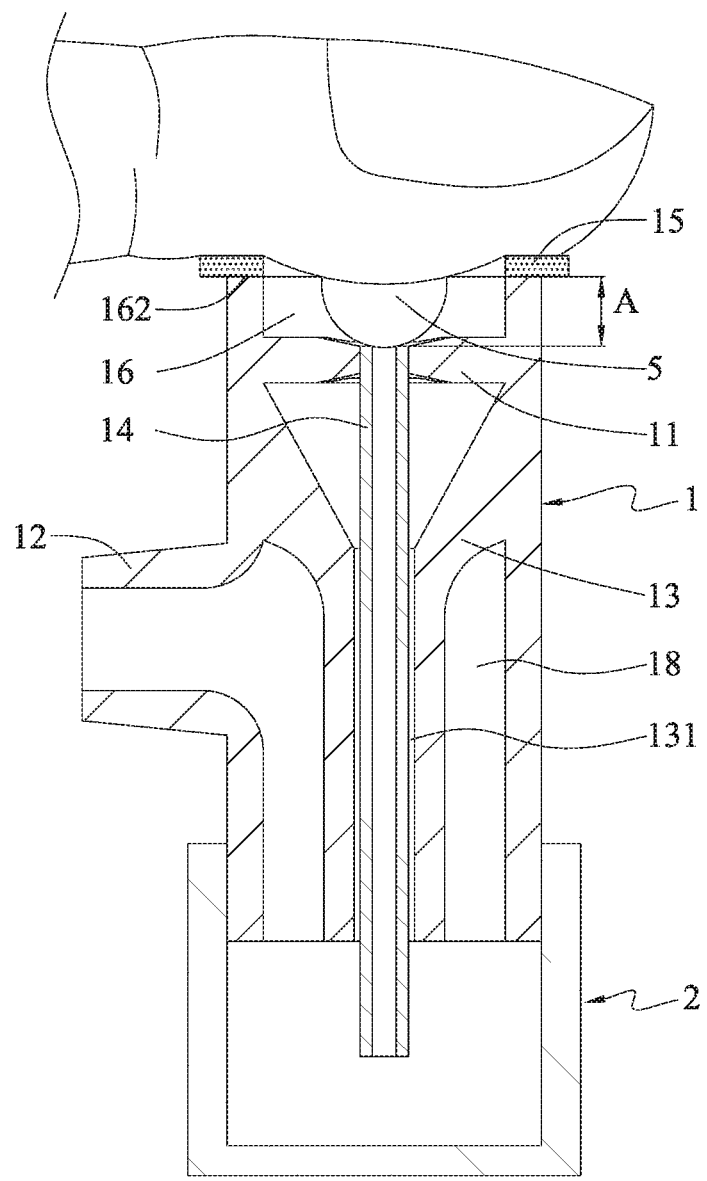
FIG. 4 illustrates a cross-sectional view of the operation of the device in accordance with the first embodiment of the present disclosure.

In FIG. 4, a finger is punctured and placed on the top window (16) of the collection unit (1). A puncture of the finger can be aimed to the top end of the capillary tube (14), such that a blood drop (5) can be released from the puncture easily. An elastic pad (15) is adapted to fit on the top surface (162) of the collection unit (1) by providing an air-tight condition to ensure the generation of a negative pressure environment in the channel (18). The pad (15) can also be a heater or an analogue to increase the bleeding by keeping the puncture site warm. Noticeably, the finger pulp punctured is partially pulled into the top window (16) under various negative pressures. In addition, a distance (A) between the top end of the capillary tube (14) and a top surface (162) of the collection unit (1) was in a range of 1.0 mm to 5.0 mm, preferably 1.5 mm to 4.5 mm, more preferably 2.0 mm to 4.0 mm. Wherein, the distance (A) suggested ensures the blood drop (5) contacting the top end of the capillary tube (14) for a better releasing of the blood drop (5). Specifically, when the blood drop (5) contacts the top end of the capillary tube (14), a surface tension of the blood drop (5) is disrupted to allow the blood (5) flowing inside or along the capillary tube (14) into the storage unit (2). If the blood drop (5) falls in the funnel structure (13) instead, the blood drop (5) can still flow into the storage unit (2) through the space (131) between the capillary tube (14) and the funnel structure (13). The vacuum connector (12) is connected to a pressure control unit (3) (shown in FIG. 9) to remove air from the channel (18) in order to create a predefined alternating negative pressure in the channel (18). Based on our observations, alternating negative pressure will facilitate pumping fingertip blood from a puncture. Moreover, the storage unit (2) in the first embodiment is detachable for delivering the collected blood sample (5) for following examinations.

Figure 5A:
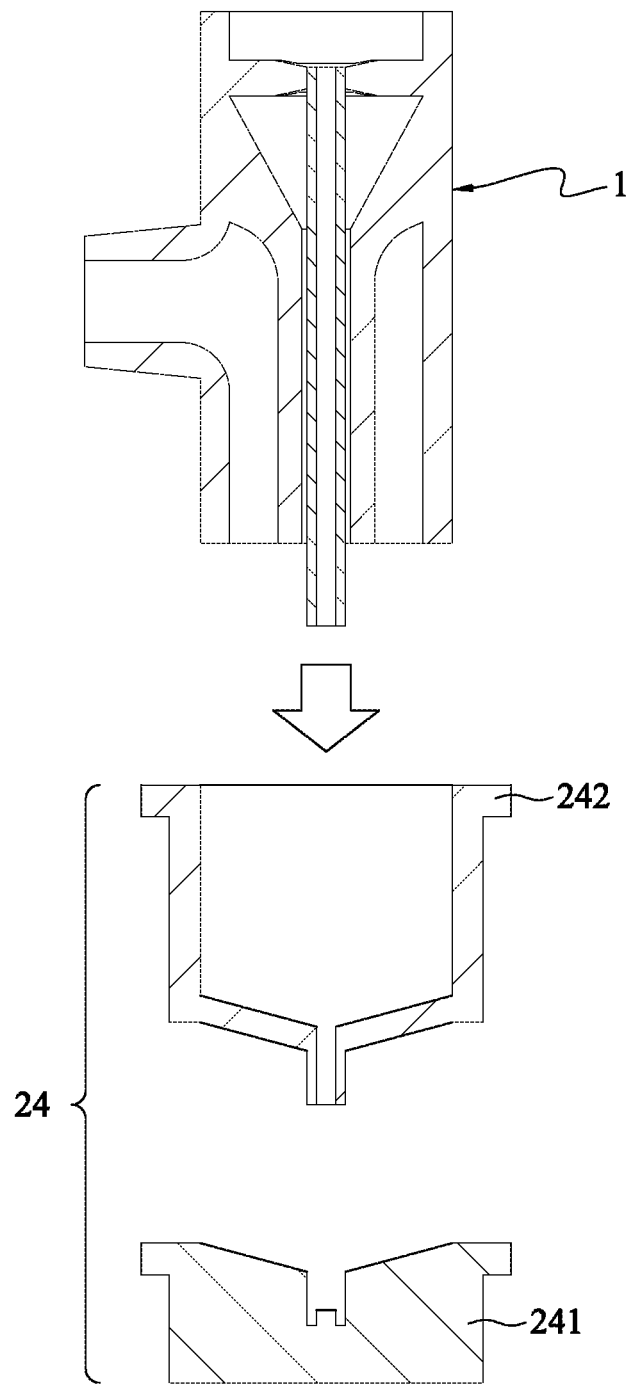
FIGS. 5A-5G illustrate cross-sectional views of a device for collecting a blood sample in accordance with a second embodiment of the present disclosure.
Figure 5B:
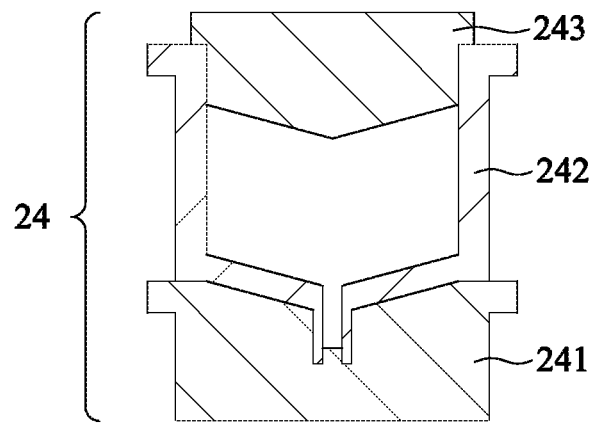
Figure 5C:
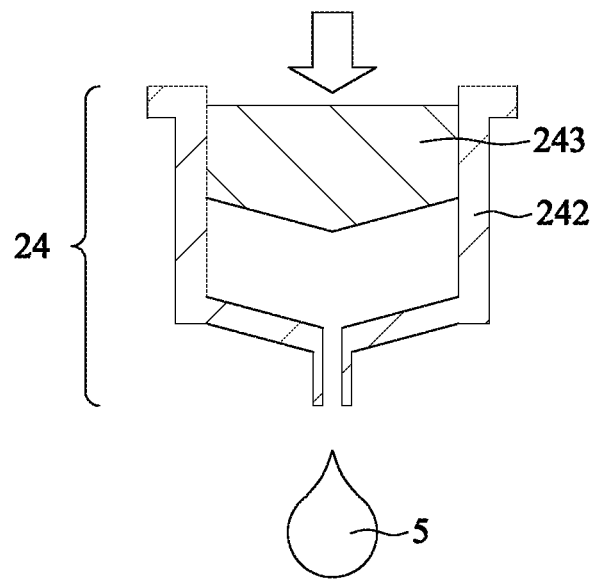
Figure 5D:
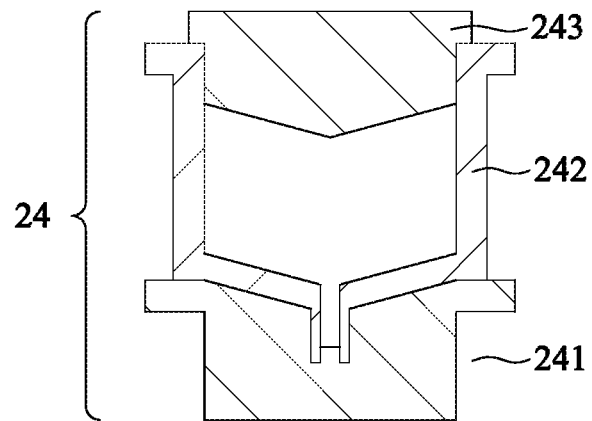
Figure 5E:
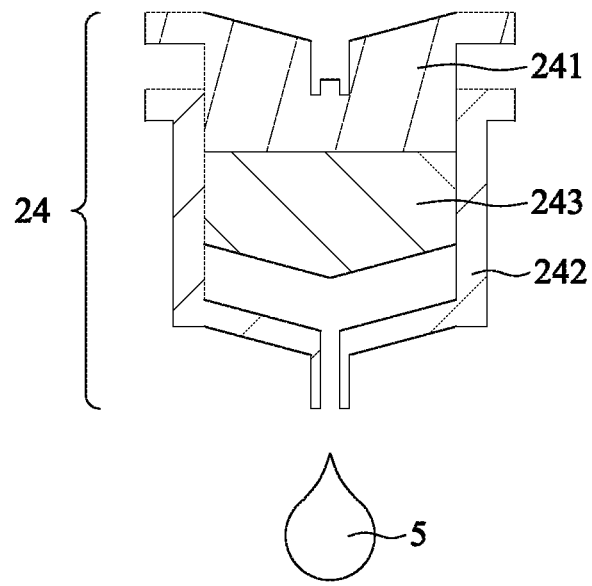
Figure 5F:
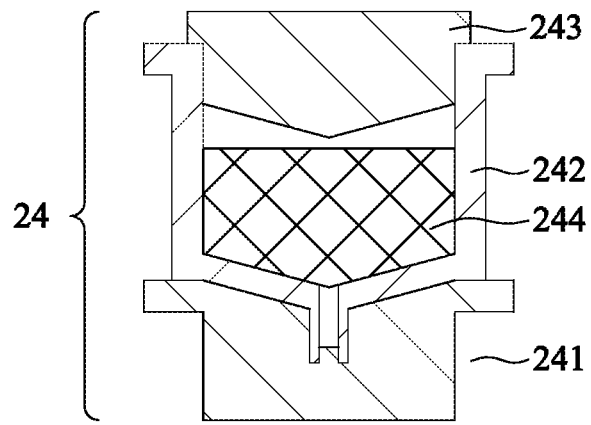
Figure 5G:
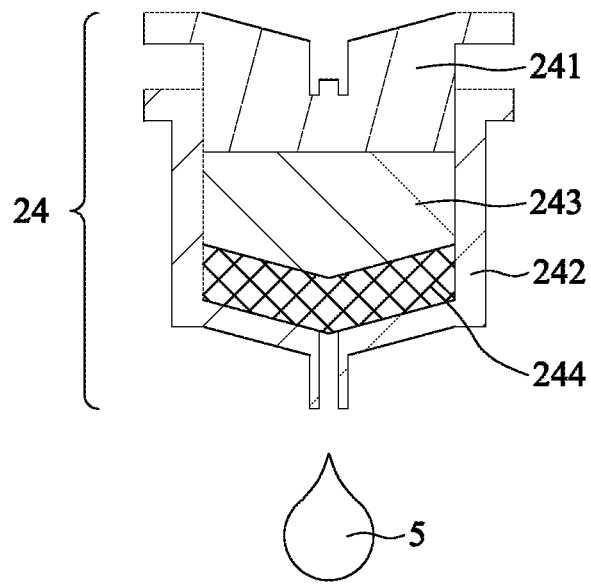

FIG. 5A shows second embodiment of the present disclosure, in which the storage unit (2) (see FIG. 4) can be transformed into a syringe-like storage unit (24), having a cap (241) and a barrel (242), for delivering and dispensing collected blood sample (5) easily. FIGS. 5B and 5C show another variant of the second embodiment. The syringe-like storage unit (24) further comprises an elastic stopper (243) for plugging an opening of the barrel (242) so as to prevent the blood sample (5) in the barrel (242) from being contaminated. After the removal of the cap (241), the deformable stopper (243) can be pressed into the barrel (242), so that the blood sample (5) in the barrel (242) can be dispensed. Moreover, the cap (241) shown in FIGS. 5D and 5E can be used as a plunger to plug into the barrel (242) to further press against the stopper (243). In FIGS. 5F and 5G, an absorbent material (244) is placed inside the barrel (242) to absorb blood sample (5) collected.

Figure 6:
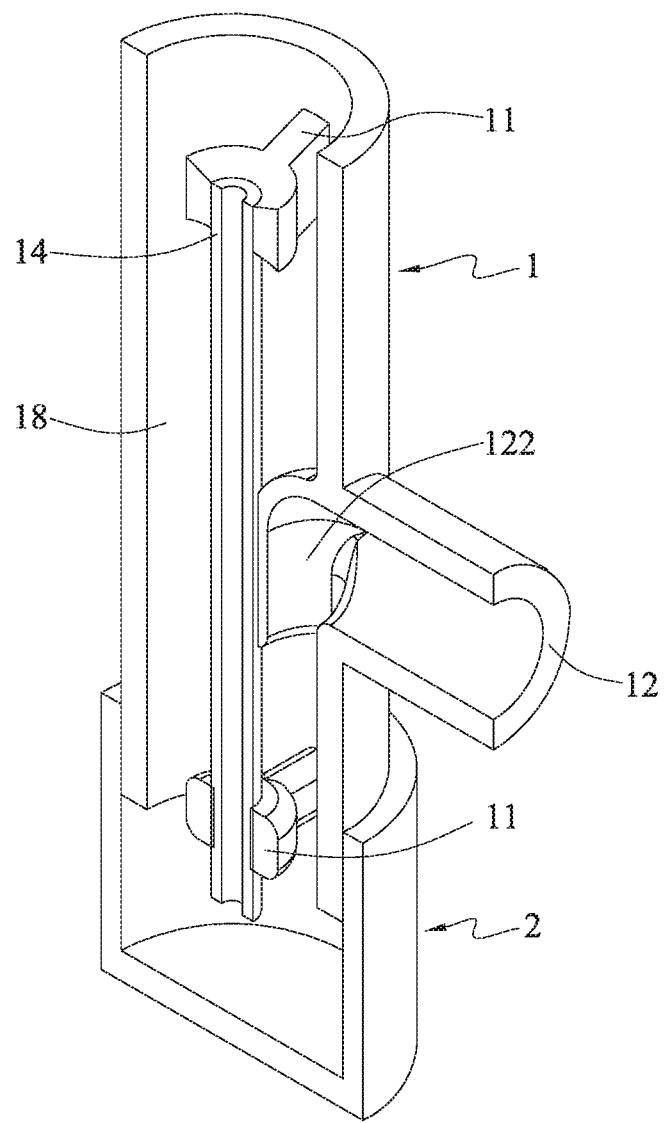
FIG. 6 illustrates an isometric view of a device for collecting a blood sample in accordance with a third embodiment of the present disclosure.

FIG. 6 shows third embodiment of the present disclosure. The elements and effects of the third embodiment similar to those of the first embodiment are herewith omitted for conciseness, and only the different parts are described. In this embodiment, the funnel structure (13, see FIG. 3) is omitted, and two holders (11) are provided to hold the capillary tube (14). A partition plate (122) in the channel

(18) is designed to prevent collected blood sample (5) from flowing to the pressure control unit (3, see FIG. 9) via the vacuum connector (12).

Figure 7:
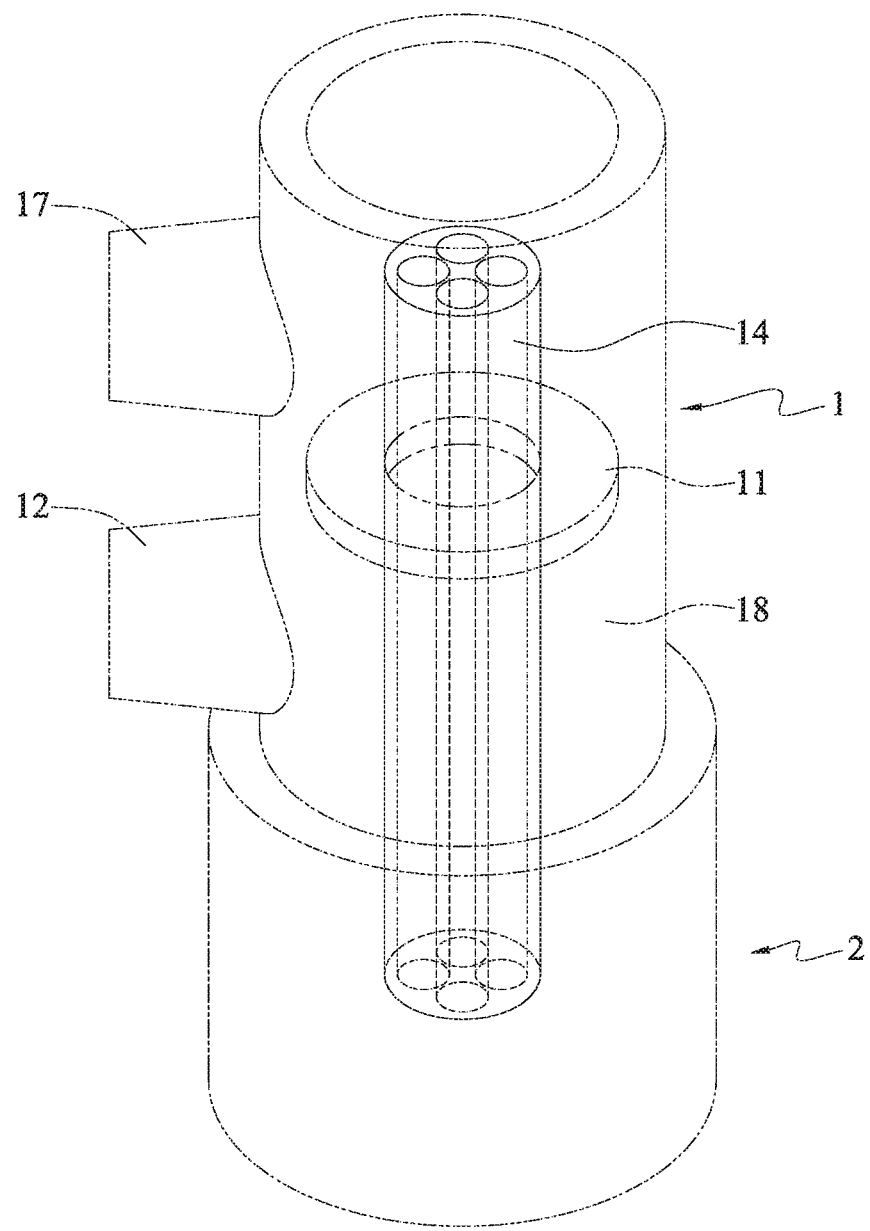
FIG. 7 illustrates a partial perspective view of a device for collecting a blood sample in accordance with a fourth embodiment of the present disclosure.

FIG. 7 shows fourth embodiment of the present disclosure. A single capillary tube (14) is replaced with multiple capillary tubes (14) to form a bunch of capillary tubes (14). The holder (11) holds the bunch of the capillary tubes (14). The channel (18) is divided into an upper part and a lower part by the holder (11). The holder may be replaced by the funnel structure (13, shown in FIG. 3), or an analogue. The upper part and the lower part are communicated through the bunch of the capillary tubes (14). While the vacuum connector (12) is communicated with the lower part of the channel (18), a venting connector (17) is communicated with the upper part of the channel (18). The vacuum connector (12) and the venting connector (17) are both connected to a pressure control unit (3, shown in FIG. 9), which comprises a vacuum unit (31) and a venting unit (32) (see FIG. 9). The vacuum unit (31) comprises a pump or other mechanisms, while the venting unit (32) comprises a valve or other mechanisms. When the vacuum unit (31) removes the air through the vacuum connector (12), the venting unit (32) is switched to create an alternating negative pressure environment inside the channel (18). Specifically, the venting unit (32) is alternatively switched to control air flowing into the upper part of the channel (18), so that the blood sample (5) remained in the bunch of the capillary tubes (14) is driven to the storage unit (2) by a pressure difference between the upper part and the lower part.

Figure 8:
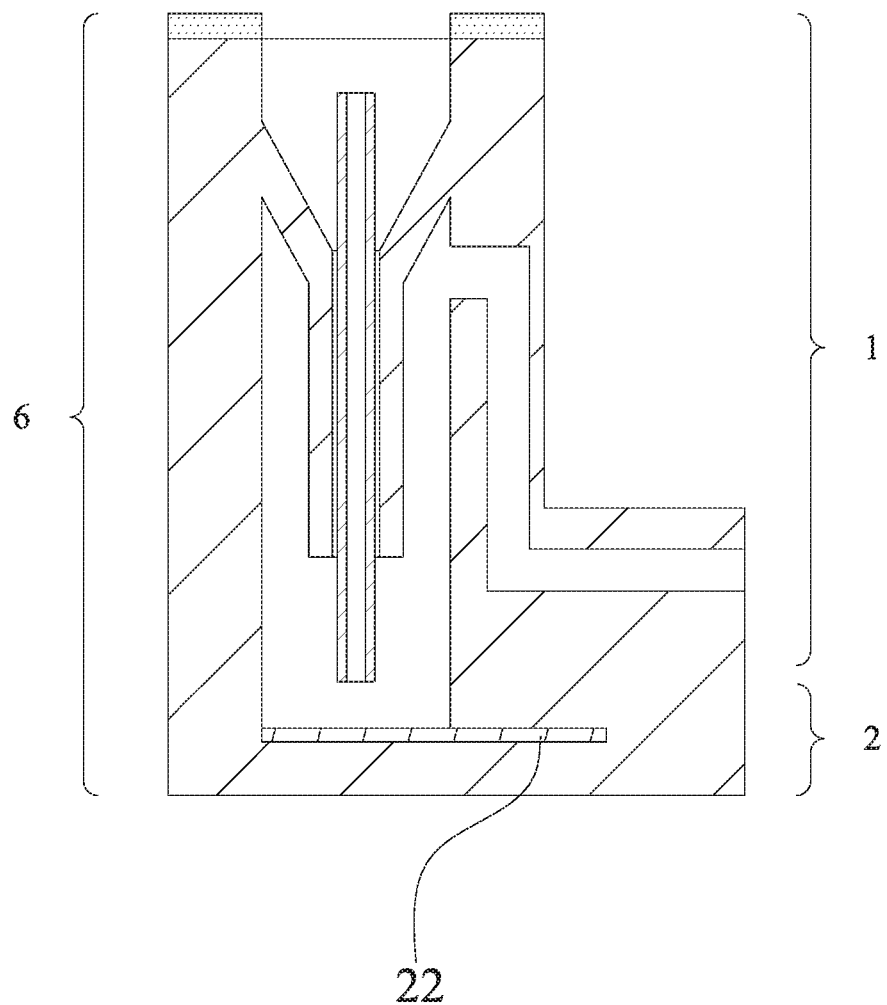
FIG. 8 illustrates a cross-sectional view of a device for collecting a blood sample in accordance with a fifth embodiment of the present disclosure.

In FIG. 8, fifth embodiment of the present disclosure is illustrated. The elements and effects of the fifth embodiment similar to the first embodiment (FIGS. 2 to 4) are herewith omitted for conciseness and only the different parts are described. In FIG. 8, the collection unit (1) and the storage unit (2) are integrated into one cartridge (6). The collection unit (1) in this embodiment (FIG. 8) can be transformed into the collection unit (1) of the third embodiment (FIG. 6), that of the fourth embodiment (FIG. 7), an analogue, or any combination thereof. Furthermore, the storage unit (2) in this embodiment, which is non-detachable from the collection unit (1), comprises a storage channel (22), a storage well, an absorbent material (244, see FIG. 10), an analogue, or any combination thereof.

Figure 9:
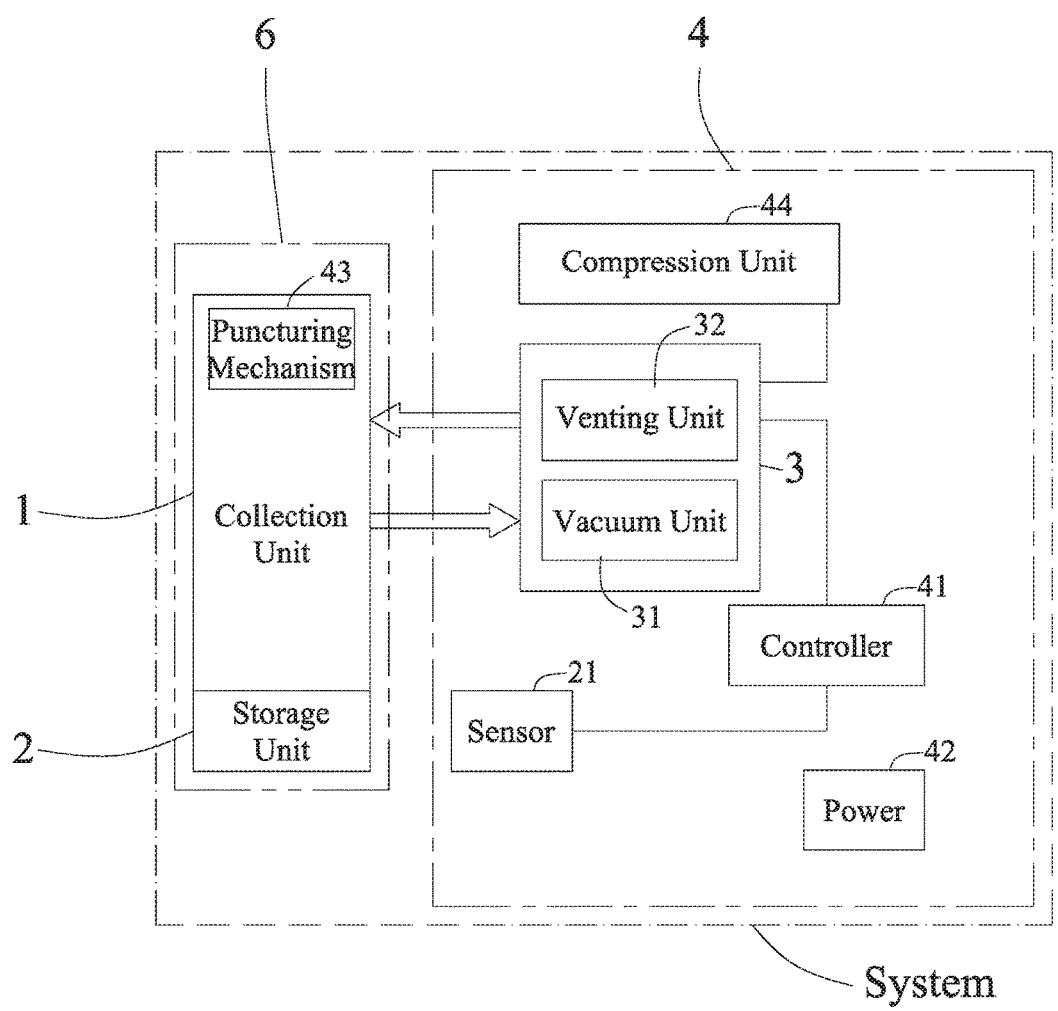
FIG. 9 illustrates a functional block diagram of a system for collecting a blood sample.
Figure 10:
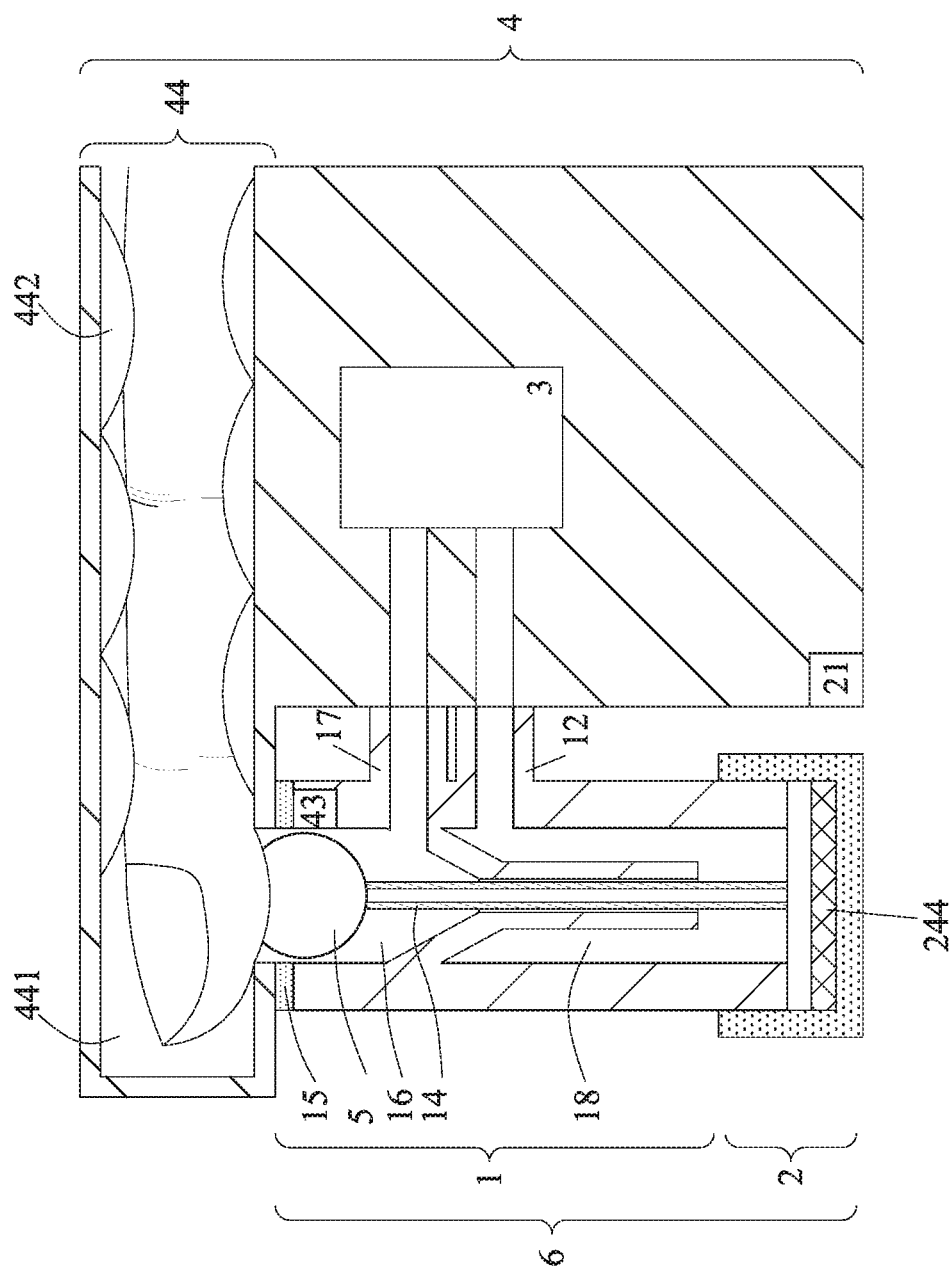
FIG. 10 illustrates a cross-sectional view of a system for collecting a blood sample in accordance with a sixth embodiment of the present disclosure.

FIG. 9 shows a functional block diagram of a blood collecting system, while FIG. 10 shows sixth embodiment of the system. The system comprises a cartridge (6) and a docking station (4). The cartridge (6) comprises a collection unit (1) and a storage unit (2) which are removable from the docking station (4). The collection unit (1) and the storage unit (2) of this embodiment can be transformed into the embodiments as shown in FIGS. 2-7, an analogue, or any combination thereof. The collection unit (1) comprises at least one capillary tube (14), a vacuum connector (12), and a pad (15). Moreover, the collection unit (1) further comprises a puncturing mechanism (43) disposed adjacent to the top window (16), wherein the puncturing mechanism (43) comprises a telescopic tip for puncturing a finger. Furthermore, the storage unit (2) is detachable from the collection unit (1). The storage unit (2) comprises a tube, a tank, a vessel, a syringe-like storage unit (24), an analogue, or any combination thereof. Extensively, an absorbent material (244) is placed inside the storage unit (2) to absorb blood sample (5) collected.

The docking station (4) comprises a pressure control unit (3). The pressure control unit (3) comprising a vacuum unit (31) and a venting unit (32) is connected with both the vacuum connector (12) and the venting connector (17) to create an alternating negative pressure. Herein, the vacuum unit (31) can be a pump or an analogue for removing the air in the channel (18). The venting unit (32) can be a valve or an analogue.

The docking station (4) further comprises a controller (41) and a power (42). The controller (41) is used to control all electronic components in the blood collecting system, especially, controlling the pressure control unit (3) to create an alternating negative pressure in the channel (18).

Additionally, the docking station (4) further comprises at least one sensor (21) to detect the volume of the collected blood sample (5). The sensor (21) can be an optical sensor, an ultrasonic sensor, a humidity sensor, an impedance sensor, a capacitance sensor, a weight sensor, or any feasible sensor as needed. When a sufficient volume of the collected blood sample (5) is detected by the sensor (21), the pressure control unit (3) is switched off to stop the creation of a negative pressure inside the channel (18).

Extensively, the docking station (4) further comprises a compression unit (44) for squeezing fingertip to obtain a blood sample (5) from the puncture (FIG. 10). The compression unit (44) includes a passage (441) above the collection unit (1) allowing a placement of a finger. The compression unit (44) also includes a plurality of air cuffs (442) arranged along the passage (441). The air cuffs (442) are connected to the pressure control unit (3), so that the air cuffs (442) will be aerated to compress the finger for accelerating bleeding from the puncture. The air cuffs (442) can be replaced by, for example but not limited to, eccentrics, aeratable bags, or finger clips.

Figure 11:
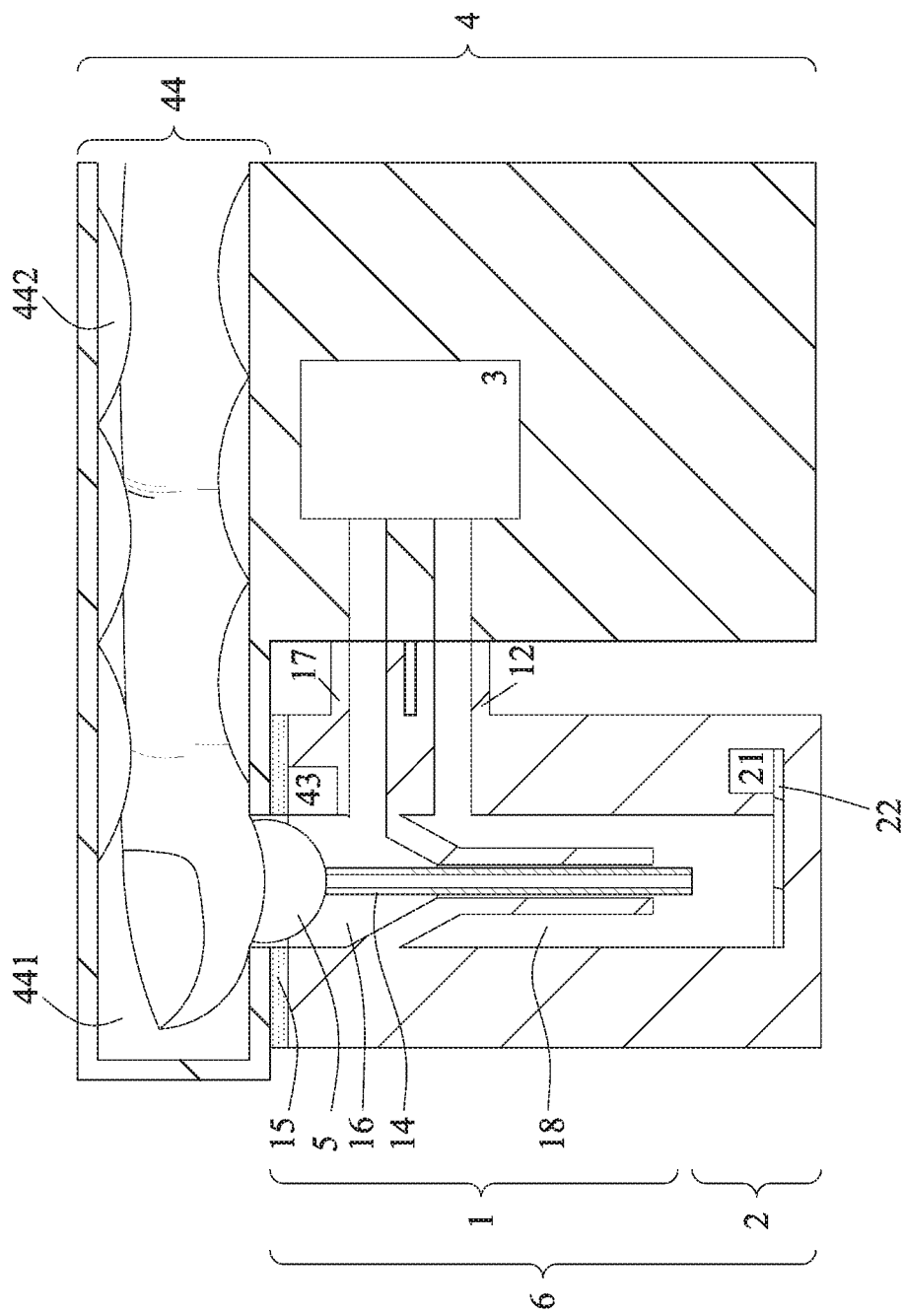
FIG. 11 illustrates a cross-sectional view of a system for collecting a blood sample in accordance with the seventh embodiment of the present disclosure.

FIG. 11 shows seventh embodiment, a variant of the blood collecting system. The elements and effects of the seventh embodiment similar to those of the sixth embodiment (shown in FIG. 10) are herewith omitted for conciseness, and only the different parts are described. In this embodiment, the collection unit (1) and the storage unit (2) are inseparable. The storage unit (2) comprises a storage channel (22), a storage well, an absorbent material (244), an analogue, or any combination thereof. In addition, at least one sensor (21) mounted adjacent to the storage unit (2) in the cartridge (6) is used to detect the volume of the collected blood sample (5).

Additionally, a method for collecting blood sample (5) of the present disclosure is described as follows. The method includes:

causing a puncture on a finger pulp either by a puncturing mechanism (43) (see FIG. 10) or a conventional lancet;

providing a top window (16) for accommodating the puncture;

providing a pad (15) to provide a tight contact between the finger and the collection unit (1), or to warm the puncture site;

providing at least one capillary tube (14) in the collection unit (1) having a top end adjacent to the top window (16) of the collection unit (1), such that a blood drop (5) from the puncture enters and flows inside or along the at least one capillary tube (14), wherein a distance (A, see FIG. 4) between the top end of the at least one capillary tube (14) and the top surface (162) of the collection unit (1) was in a range of 1.0 mm to 5.0 mm, preferably 1.5 mm to 4.5 mm, more preferably 2.0 mm to 4.0 mm;

creating a negative pressure within the channel (18) (see FIG. 10) by removing air from the channel (18) through the vacuum connector (12) connected to the pressure control unit (3);

the negative pressure mentioned above is further controlled to create an alternating negative pressure in conjunction with the venting connector (17), herein the alternating negative pressure is in a range of −10 kPa to −80 kPa, preferably −201 cPa to −60 kPa, more preferably −401 cPa to −50 kPa;

providing a compression unit (44) placed above the collection unit (1) for squeezing fingertip to obtain blood (5) from the puncture;

collecting a specific volume of blood (5) using at least one sensor (21) in conjunction with controlling the negative pressure, wherein the volume of blood (5) collected was less than or equal to 1 ml; and storing the blood (5) collected in the storage unit (2), herein the blood (5) in the storage unit (2) (see FIGS. 10 and 11) can be delivered for various applications.

The present disclosure has been described using exemplary embodiments to illustrate the principles and the effects of the present disclosure, but not intend to limit the present disclosure. The present disclosure without departing from the spirit and scope of the premise can make various changes and modifications by a person skilled in the art. Therefore, the scope of protection of the rights of the disclosure, the claim should be listed in the book. Therefore, the scope of the disclosure should be defined by the appended claims.

What is claimed is:

1. A device for collecting a blood sample, comprising:
   a collection unit comprising:
   a top window;
   a top surface;
   a channel communicated with the top window;
   at least one capillary tube having a top end adjacent to the top window;
      wherein a distance between the top end of the at least one capillary tube and the top surface of the collection unit is in a range of 1.0 mm to 5.0 mm, such that the top end of the at least one capillary tube is used to contact with a blood drop from a puncture to continuously draw the blood flowing inside or along the at least one capillary tube into a storage unit by disrupting a surface tension of the blood drop, and
      a vacuum connector communicated with the channel, extended outwardly from the collection unit, and connected to a pressure control unit to remove air from the channel and create an alternating negative pressure in the channel; and
      the storage unit disposed under the collection unit.

2. The device of claim 1, further comprising a pad disposed on the top surface of the collection unit.

3. The device of claim 1, wherein the collection unit further comprises a funnel structure surrounding the at least one capillary tube.

4. The device of claim 1, wherein the collection unit further comprises at least one holder holding the at least one capillary tube.

5. The device of claim 1, wherein the at least one capillary tube is replaced with multiple capillary tubes to form a bunch of capillary tubes.

6. The device of claim 1, wherein the vacuum connector comprises a partition plate inside the collection unit and extended toward the storage unit.

7. The device of claim 1, wherein the collection unit further comprises a venting connector communicated with the channel and connected to the pressure control unit to create the alternating negative pressure in the channel.

8. The device of claim 1, wherein the storage unit comprising a tube, a tank, a vessel, a syringe-like storage unit, an analogue, or any combination thereof is detachable from the collection unit for delivering the blood sample.

9. The device of claim 1, wherein the storage unit comprising a storage channel, a storage well, an absorbent material, an analogue, or any combination thereof is non-detachable from the collection unit.

10. A system for collecting a blood sample, comprising:
    a cartridge comprising the collection unit and the storage unit according to claim 1; and
    a docking station comprising a pressure control unit.

11. The system of claim 10, wherein the cartridge is removable from the system.

12. The system of claim 10, wherein the collection unit further comprises a puncturing mechanism adjacent to the top window of the collection unit.

13. The system of claim 10, further comprising a pad disposed on the top surface of the collection unit.

14. The system of claim 10, wherein the collection unit further comprises a funnel structure surrounding the at least one capillary tube.

15. The system of claim 10, wherein the at least one capillary tube is replaced with multiple capillary tubes to form a bunch of capillary tubes.

16. The system of claim 10, wherein the vacuum connector comprises a partition plate inside the collection unit and extended toward the storage unit.

17. The system of claim 10, wherein the collection unit further comprises a venting connector communicated with the channel and connected to the pressure control unit to create the alternating negative pressure in the channel.

18. The system of claim 10, wherein the storage unit comprising a tube, a tank, a vessel, a syringe-like storage unit, an analogue, or any combination thereof is detachable from the collection unit for delivering the blood sample.

19. The system of claim 10, wherein the storage unit comprising a storage channel, a storage well, an absorbent material, an analogue, or any combination thereof is non-detachable from the collection unit.

20. The system of claim 10, further comprising at least one sensor configured to detect a volume of the blood sample.

21. The system of claim 10, further comprising a compression unit disposed above the collection unit for compressing a finger of a user.

22. A method of collecting a blood sample, comprising:
    providing a collection unit having a top window, a top surface, and a channel communicated with the top window;
    providing at least one capillary tube in the collection unit having a top end adjacent to the top window for guiding a blood drop from the puncture to flow inside or along the at least one capillary tube, wherein a distance between the top end of the at least one capillary tube and the top surface of the collection unit is in a range of 1.0 mm to 5.0 mm, such that the top end of the at least one capillary tube is used to contact with a blood drop from a puncture to continuously draw the blood flowing inside or along the at least one capillary tube into a storage unit by disrupting a surface tension of the blood drop;
    removing air from the channel through a vacuum connector to create an alternating negative pressure in the channel by connecting the channel and a pressure control unit, wherein the vacuum connector is communicated with the channel and is extended outwardly from the collection unit; and storing the blood sample in the storage unit disposed underneath the collection unit.

23. The method of claim 22, further comprising providing a pad on the top surface of the collection unit for a tight contact or warming a puncture site.

24. The method of claim 22, wherein the negative pressure is in a range of −10 kPa to −80 kPa.

25. The method of claim 22, wherein the alternating negative pressure is created in the channel by connecting the channel and the pressure control unit via a venting connector.

26. The method of claim 22, further comprising collecting a specific volume of the blood sample using at least one sensor in conjunction with controlling the negative pressure in the channel.

27. The method of claim 22, further comprising squeezing a fingertip of a user with a compression unit disposed above the collection unit to obtain the blood sample from the puncture.

* * * * *